United States Patent [19]

Whitford

[11] Patent Number: 4,550,831
[45] Date of Patent: Nov. 5, 1985

[54] STRIP OF DETACHABLY CONNECTED BAGS FOR MEDICAL SUPPLIES

[75] Inventor: Alan Whitford, North Scituate, R.I.

[73] Assignee: Superior Plastic Products Corp., Cumberland, R.I.

[21] Appl. No.: 598,181

[22] Filed: Apr. 9, 1984

[51] Int. Cl.⁴ .................................................. B65D 33/22
[52] U.S. Cl. ..................... 206/439; 383/37; 383/41; 383/66
[58] Field of Search .................. 206/439; 383/37, 41, 383/66

[56] References Cited

U.S. PATENT DOCUMENTS

| | | | |
|---|---|---|---|
| 2,997,224 | 8/1961 | Stannard | 206/439 |
| 3,254,828 | 6/1966 | Lerner | 383/37 |
| 3,685,720 | 8/1972 | Brady | 206/439 |
| 3,761,013 | 9/1973 | Schuster | 206/439 |
| 3,819,106 | 6/1974 | Schuster | 206/439 |
| 3,938,658 | 2/1976 | Rohde | 206/439 |
| 4,367,816 | 1/1983 | Wilkes | 206/439 |
| 4,401,213 | 8/1983 | Lerner | 383/37 |
| 4,417,658 | 11/1983 | Gardner et al. | 383/66 |

Primary Examiner—Stephen P. Garbe
Attorney, Agent, or Firm—Salter & Michaelson

[57] ABSTRACT

A strip of detachably connected bags for receiving and containing medical supplies and the like includes a plurality of substantially identical bags which are detachably connected in end-to-end relation. Each of the bags includes a seamless tubular wall portion which is sealed at one end thereof and open at the opposite end thereof and has an elongated longitudinally extending slit therein, and an access strip which is preferably made of a semipermeable material is adhered to the exterior of the wall portion for covering the slit. The bags are only connected along one side of the wall portions thereof so that they can be filled while they are still connected utilizing an automated feeding apparatus. After the bags have been filled and the open ends thereof have been sealed, the access strips provide quick access to articles in the bags; and when the access strips are made of a semipermeable material, they allow sterilizing gases to be introduced into the interiors of the bags for sterilizing the articles contained therein.

2 Claims, 4 Drawing Figures

STRIP OF DETACHABLY CONNECTED BAGS FOR MEDICAL SUPPLIES

BACKGROUND AND SUMMARY OF THE INVENTION

The instant invention relates to packaging for medical equipment and supplies and more particularly to an elongated strip of detachably connected bags for receiving and containing medical equipment and supplies and the like prior to the use thereof.

Various types of packaging, such as various types of hermetically sealable bags, have been heretofore available for receiving and containing medical equipment and the like under sterilized conditions prior to the use thereof. In addition, various types of packaging have been available which have been adapted to permit the sterilization of articles contained therein and to thereafter maintain the articles under sterilized conditions. For example, sealable plastic bags and other types of plastic packaging having side access openings therein which are sealingly covered with detachable access strips made of semipermeable or "breathable" materials have been heretofore available. Packaging of this type has permitted the sterilization of articles contained therein through the use of various types of sterilizing gases which can pass through the breathable strips of the bags after they are sealed to sterilize articles contained therein. The U.S. Pat. No. 3,472,369 to Schuster discloses packaging which is generally exemplary in this regard and represents prior art which is generally related to the instant invention. The packaging disclosed in Schuster is, however, believed to be only of general interest, since it is made from a flat sheet of plastic material which is folded to a desired configuration, and, as a result, it is not really adapted for continuous automated manufacturing and/or feeding operations.

Other types of packaging which have comprised a flexible plastic tubular wall portion which is sealed at one end thereof and has a longitudinally extending slit on one side thereof, and a semipermeable strp which is sealed to the exterior of the wall portion for covering the slit have also been heretofore available. Bags of this type have had the advantage that they can be effectively heat sealed along the open ends thereof after articles have been placed therein. Further, when bags of this type are heat sealed, the seals are only required to penetrate two layers of plastic material, and therefore effective uniform seals can easily be formed. Individual bags of this type, however, have the disadvantage that they also are only adapted for unautomated individual article feeding operations.

The instant invention provides an effective continuous strip of bags which can be used by conventional automated feeding apparatus for filling, sealing and separating the bags of the strip in a continuous automated operation. The strip of connected bags of the instant invention comprises a plurality of substantially identical bags, each comprising a seamless tubular wall portion made of a flexible plastic material which is in a substantially flattened two-sided configuration and has an elongated slit along one side thereof, and is sealed at one end thereof and open at the opposite end thereof, and a detachable strip which is received on the wall portion for covering the slit. The slit in the wall portion extends substantially longitudinally from a point which is spaced from the open end thereof to a point which is spaced from the sealed end thereof, and the detachable strip extends longitudinally along the exterior of the wall portion so that it covers the slit, and it is heat sealed to the wall portion adjacent the opposite edges of the slit and adjacent the end of the slit which is closest to the sealed end of the wall portion. The bags are detachably connected along perforate lines in end-to-end relation so that the sealed end of the wall portion of one bag is detachably connected to the open end of the wall portion of the next bag. However, the bags are detachably connected along only one side of the wall portion of open end of each bag so that access to the interiors of the bags is provided through the open ends thereof while the bags are connected. Further, in the preferred embodiment of the invention, the detachable strips on the bags extend along substantially the entire extents of the respective bags, and the slits in the bags are provided along the sides thereof which are connected so that the detachable strips are also disposed on the connected sides of the bags. Further, preferably the detachable strips are also detachably connected at the ends thereof, and the detachable strips are preferably constructed of a breathable material, such as paper or a spun polyolefin, for example, Tyvek (duPont TM).

The strip of connected bags of the instant invention is particularly effective from a manufacturing standpoint since it can be manufactured in an automated operation from an elongated tubular plastic strip and an elongated strip of a spun polyolefin or paper. In particular, the tubular plastic strip can easily be heat sealed, slit and perforated in a continuous automated operation to form individual connected bag wall portions, and the paper or polyolefin access strip can easily be applied in a continuous operation so that it covers the slits of the bags. Because of the configurations of the bags, all of the heat seals which are applied to define the ends thereof are relatively uniform seals which uniformly encompass only two layers of plastic material. Further, because of the way in which the individual bags are connected, they can be filled automatically before they are separated, and the access strips on the bags provide easy access to the interiors thereof after the bags have been separated and sealed, and in the preferred embodiment, they also provide a means for introducing sterilizing gases into the interiors of the bags for sterilizing the articles contained therein.

Accordingly, it is a primary object of the instant invention to provide an effective strip of detachably connected bags, of the type having detachable access strips thereon, wherein the strip can be effectively manufactured in an automated operation.

Another object of the instant invention is to provide an effective strip of detachably connected bags which is adapted for automated feeding operations wherein the bags are of the type having detachable access strips thereon.

A still further object of the instant invention is to provide an effective strip of connected bags which is adapted for automated feeding operations, wherein the bags are of the type which have breathable strips thereon for sterilizing articles contained therein utilizing sterilizing gases.

Other objects, features and advantages of the invention shall become apparent as the description thereof proceeds when considered in connection with the accompanying illustrative drawings.

DESCRIPTION OF THE DRAWING

In the drawings which illustrate the best mode presently contemplated for carrying out the present invention.

DESCRIPTION OF THE INVENTION

Figure 1:
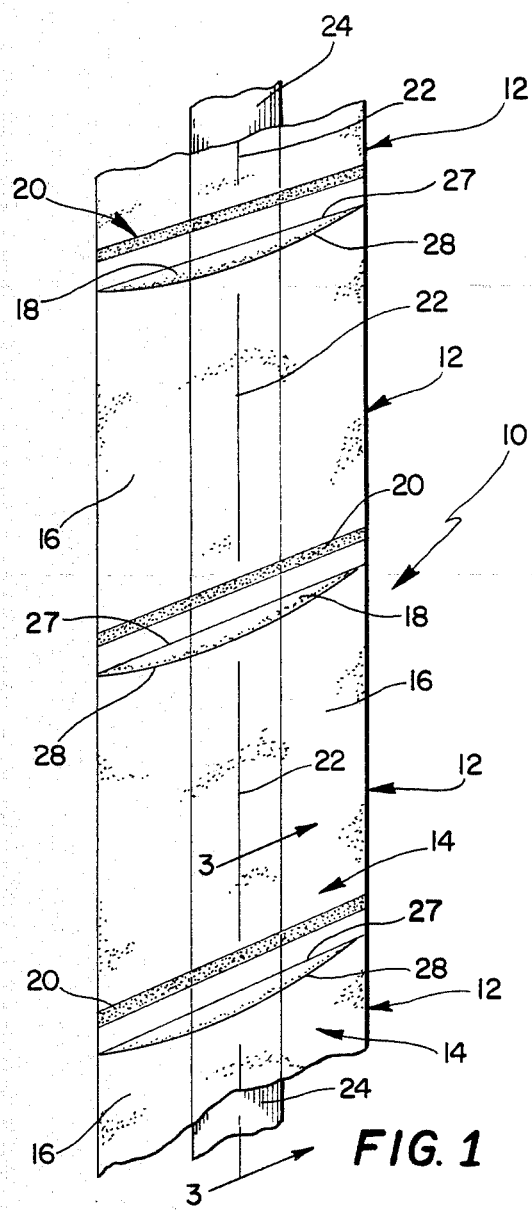
FIG. 1 is a perspective view of the strip of connected bags of the instant invention.
Figure 2:
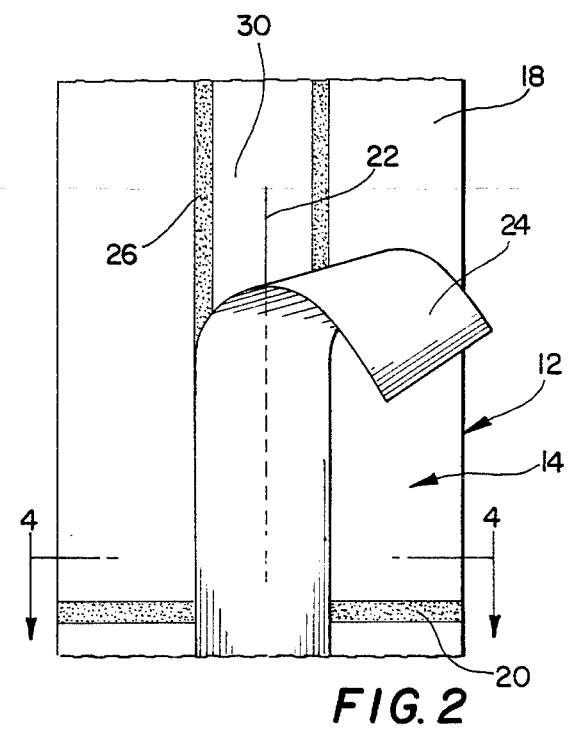
FIG. 2 is a plan view of a single bag with the detachable strip thereof partially removed.
Figure 4:
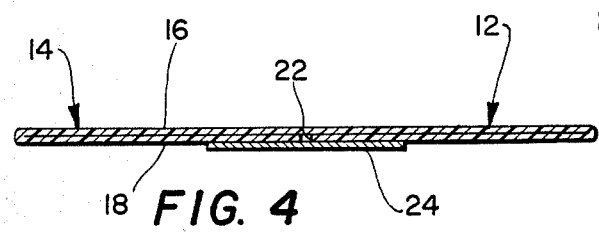
FIG. 4 is a sectional view taken along line 4—4 in FIG. 2.
Figure 3:
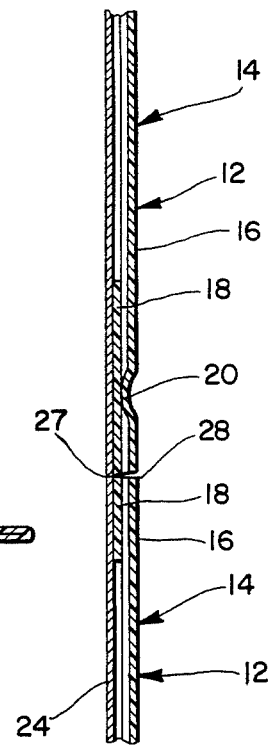
FIG. 3 is a sectional view taken along line 3—3 in FIG. 1.

Referring now to the drawing, the strip of connected bags of the instant invention is illustrated and generally indicated at 10 in FIG. 1. The strip 10 comprises a plurality of individual bags generally indicated at 12 in FIGS. 1 through 4 which are connected at the ends thereof and which are adapted to be constructed in an automated manufacturing operation and also adapted to receive articles therein in an automated feeding operation.

Each of the bags 12 in the strip 10 comprises a seamless tubular wall portion 14 which is preferably constructed of a flexible, transparent plastic material, such as polyethylene, and which is preferably folded to a substantially flattened configuration to provide first and second sides 16 and 18, respectively, of each of the wall portions 14. Each of the wall portions 14 has a substantially transversely extending seal 20 at one end thereof and is open at the opposite end thereof, and a substantially longitudinally extending slit 22 is provided in the second side 18 of each of the wall portions 14. Each of the slits 22 extends from a point which is spaced from the seal 20 of the respective wall portion 14 to a point which is spaced from the opposite or open end of the respective wall portion 14. Also provided in each of the bags 12 is a detachable access strip 24 which is preferably constructed of a semipermeable or breathable material, such as a spun polyolefin or paper. For example, a spun polyolefin such as Tyvek (duPont TM) has been found to be an effective material for the strips 24. Each of the strips 24 is detachably sealed to the second side 18 of the respective wall portion 14 for covering the respective slit 22. In this regard, preferably a conventional water or lacquer based heat-seal adhesive is used for sealing the strips 24 to the exterior sides 18 of the wall portions 14 in areas 26 which extend along the opposite sides of the slits 22 and along the ends of the slits 22 which are closest to the seals 20 of the respective wall portions 14. Further, in the preferred embodiment, the portions of the areas 26 which extend along the sides of the slits 22 are preferably spaced outwardly from the slits 22 so that the strips 24 are sealed to the sides 18 in the peripheral side areas of the strips 24. For reasons of convenience, the adhesive which is used for sealing the strips 24 to the wall portions 14 is preferably applied to the entire inner surfaces of the strips 24, and thereafer the strips 24 are adhered to the sides 18 by applying heat in the areas 26 to effect the desired heat seals. Further, when the adhesive is applied to the entire inner surfaces of the access strips 24, the portions of the seal areas 26 which extend along the ends of the slits 22 adjacent the heat seals 20 can be formed simultaneously with the seals 20 so that they actually coextend therewith. Further, when the open ends of the bags 12 are heat sealed after the bags 12 have been filled, heat-seals between the strips 24, and the wall portions 14 are simultaneously formed along the previously unsealed ends of the strips 24 to completely seal around the slits 22.

The bags 12 are detachably connected along perforate lines 27 in end-to-end relation so that the sealed end of one bag 12 is connected to the open end of the next bag 12 in the strip 14. In this regard, the bags 12 are connected along only one side of the respective wall portions 14 thereof so that exposed or unconnected edges 28 are provided on the opposite sides of the open ends of the wall portions 40. Preferably the wall portions 14 are connected along the ends of the second sides 18 thereof so that the strips 24 extend along the connected sides of the wall portions 14. The strips 24 are preferably also connected along the perforate lines 27 when the strip 10 is constructed in this manner.

The strip of connected bags 10 is particulary adapted for use in automated feeding operations wherein individual articles are mechanically introduced into the bags 12. In this regard, it has been found that the strip 10 can be effectively used in a Syntron (FMC Corp. TM) vibratory feeding system, although the use of the strip 10 in a variety of other automated bag feeding systems is contemplated. The open ends of the bags 12 permit access to the interiors thereof along the edges 28 so that components and other articles can easily be received in the bags 12. After the appropriate components or other supplies have been positioned in the bags 12, the open ends of the bags 12 can be heat-sealed adjacent the edges 28 to seal the respective sides 16 and 18 thereof together and also to seal the adjacent ends of the strips 24 to the respective sides 18 to effect complete seals around the slits 22 of the respective bags 12. After the components or pieces of equipment have been received in the bags 12 and the bags 12 have been sealed in this manner, the bags 12 can be separated from each other, and the articles contained in the bags 12 can be sterilized by exposing the bags 12 to a sterilizing gas which can pass through the strips 24. Thereafter the articles contained in the bags 12 will remain sterilized until the respective strips 24 have been removed from the bags 12 to provide access to the respective articles contained therein. In this regard, since the areas 26 are preferably spaced outwardly from the slits 22, sterilized areas 30 are provided on the exteriors of the bags 12 adjacent the slits 22, and therefore inadvertent contact with the outwardly facing areas of the sides 18 adjacent the slits 22 during the removal of articles from the bags 12 does not normally contaminate the articles.

It is seen, therefore, that the instant invention provides an effective strip of connected bags of the type used for containing medical equipment during the sterilization and storage thereof. The bags 12 of the strip 10 are adapted for automated feeding operations, and they can easily be formed in an automated process. Accordingly, for these reasons, as well as the other reasons hereinabove set forth, it is seen that the instant invention represents a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An elongated strip of connected bags for medical supplies and the like comprising a plurality of substantially identical bags, each of said bags comprising a substantially flattened, two-sided seamless tubular wall portion made of a flexxible plastic material which is sealed at one end thereof and open at the opposite end thereof, the seal at the sealed end of each of said bags being formed between the two sides of said wall portion thereof without other layers of plastic material therebetween, said wall portion of each bag having a substantially longitudinally extending slit therein which extends along one side thereof from a point spaced from the open end thereof to a point spaced from the sealed end thereof and a longitudinally extending detachable strip which extends along the exterior of said wall portion for covering said slit and which is sealingly secured to said wall portion adjacent said slit and adjacent the end of said slit closest to the sealed end of said wall portion, the slits in said bags all being on the same side of said strip of connected bags, said bags being detachably connected in end-to-end relation so that the sealed ends of the wall portions of said bags are detachably connected to the open ends of the wall portons of the next bags along only the sides of the wall portons of said bags through which said slits extend to permit access to the interiors of said bags through the open ends thereof while said bags are connected, said detachable strips on said bags also being detachably connected in end-to-end relation.

2. In the strip of connected bags of claim 1, said detachable strip on each of said bags further characterized as being breathable.

* * * * *